(12) United States Patent
Teegavarapu et al.

(10) Patent No.: US 11,618,069 B2
(45) Date of Patent: Apr. 4, 2023

(54) AUTOMATED WIRE ROD TRIMMING STATION AND SAMPLE QUALITY EVALUATION

(71) Applicant: PRIMETALS TECHNOLOGIES USA LLC, Alpharetta, GA (US)

(72) Inventors: Sudhakar Teegavarapu, Hopkinton, MA (US); Matthew D. Palfreman, Charlton, MA (US); Jason Zelle, Worcester, MA (US); William X. Shen, Boylston, MA (US)

(73) Assignee: Primetals Technologies USA LLC, Alpharetta, GA (US)

( * ) Notice: Subject to any disclaimer, the term of this patent is extended or adjusted under 35 U.S.C. 154(b) by 979 days.

(21) Appl. No.: 16/353,163

(22) Filed: Mar. 14, 2019

(65) Prior Publication Data
US 2019/0291169 A1    Sep. 26, 2019

Related U.S. Application Data

(63) Continuation-in-part of application No. 16/123,347, filed on Sep. 6, 2018, now abandoned.
(Continued)

(51) Int. Cl.
*B21F 11/00* (2006.01)
*G01N 1/04* (2006.01)
(Continued)

(52) U.S. Cl.
CPC ............. *B21F 11/00* (2013.01); *B21C 47/22* (2013.01); *B26D 7/01* (2013.01); *B26D 7/0616* (2013.01);
(Continued)

(58) Field of Classification Search
CPC ........ B21F 11/00; B21F 33/005; B21F 37/00; B25J 11/0055; B21C 47/262;
(Continued)

(56) References Cited

U.S. PATENT DOCUMENTS 3,383,803 A      5/1968 Schulte et al.
4,064,916 A *  12/1977 Dahmen ............... B21C 47/262
                                                              83/907
(Continued)

FOREIGN PATENT DOCUMENTS

DE    19846101       8/2000
DE    19846101 C1   8/2000
(Continued)

OTHER PUBLICATIONS

Translation; JP 08-110208 A, Asahi Seiki Kogyo KK; Apr. 1996.*
(Continued)

*Primary Examiner* — Edward T Tolan
(74) *Attorney, Agent, or Firm* — Gesmer Updegrove LLP

(57) ABSTRACT

An automated trimming system is provided that includes a vision system identifying the number of rings positioned within a coil and sheared positions where the rings need to be cut. One or more trimming mechanisms receive the sheared positions and proceed to cut the rings at the sheared positions. A hook arrangement interfaces with the coil for transferring the coil to a trimming area. Moreover, an automated trimming system is provided that includes a coil having a plurality of rings. One or more trimming mechanisms select a number of rings from the coil and proceed to form a sample of desired length, by cutting a portion of the rings. A receiver unit receives the sample from the one or more trimming mechanisms to evaluate the quality of the sample.

24 Claims, 12 Drawing Sheets

Related U.S. Application Data

(60) Provisional application No. 62/645,446, filed on Mar. 20, 2018.

(51) Int. Cl.
  *B21C 47/22* (2006.01)
  *G01N 33/20* (2019.01)
  *B26D 7/01* (2006.01)
  *B26D 7/06* (2006.01)
  *B26D 7/00* (2006.01)

(52) U.S. Cl.
  CPC .............. *G01N 1/04* (2013.01); *G01N 33/20* (2013.01); *B26D 2007/0012* (2013.01)

(58) Field of Classification Search
  CPC ..... B21C 47/265; G01B 11/02; G01B 11/022; B26D 5/007; B26D 5/06; B26D 5/086; B26D 7/01; B26D 7/0666; G01N 1/02; G01N 1/04; G01N 2001/085
  See application file for complete search history.

(56) References Cited

U.S. PATENT DOCUMENTS

| | | | | |
|---|---|---|---|---|
| 5,263,657 | A * | 11/1993 | Grotepass | B21C 47/24 |
| | | | | 242/363 |
| 6,227,091 | B1 | 5/2001 | Grossman et al. | |
| 6,402,074 | B1 * | 6/2002 | Shore | C21D 9/5732 |
| | | | | 242/363 |
| 2011/0239719 | A1 | 10/2011 | Kalkau et al. | |

FOREIGN PATENT DOCUMENTS

| | | | |
|---|---|---|---|
| EP | 0255724 | 2/1988 | |
| EP | 255724 A2 | 10/1988 | |
| JP | 59-94523 A * | 5/1982 | ............. B21C 47/26 |
| JP | 58-212561 A * | 12/1983 | ........... B21C 47/262 |
| JP | 60-87923 A * | 5/1985 | ............. B21C 47/00 |
| JP | H08110208 A | 4/1996 | |
| JP | 2001328023 | 11/2001 | |
| KR | 101568593 | 11/2015 | |
| RU | 2353454 C2 | 4/2009 | |
| WO | 2017082908 | 5/2017 | |
| WO | 2017082908 A1 | 5/2017 | |

OTHER PUBLICATIONS

Translation JP2001-328023A, Morimoto, Nov. 2001.*
Office Action issued by Chinese Patent Office dated Nov. 30, 2021 in related Chinese Patent Application No. 201980020383.X.
Office Action issued by Indian Patent Office dated Mar. 20, 2021 in related Indian Patent App. No. 202017038005.
Office Action and search report issued by Russian Patent Office dated Nov. 30, 2021 in related Russian Patent Application No. 2020130783.
Office Action issued by Japanese Patent Office dated Dec. 6, 2021 in related Japanese Patent Application No. 2020-550767.
International Search Report and Written Opinion in related PCT/US2019/022208 dated Jun. 13, 2019.
International Search Report and Written Opinion in related PCT/US2019/022208 dated Sep. 22, 2020.

* cited by examiner

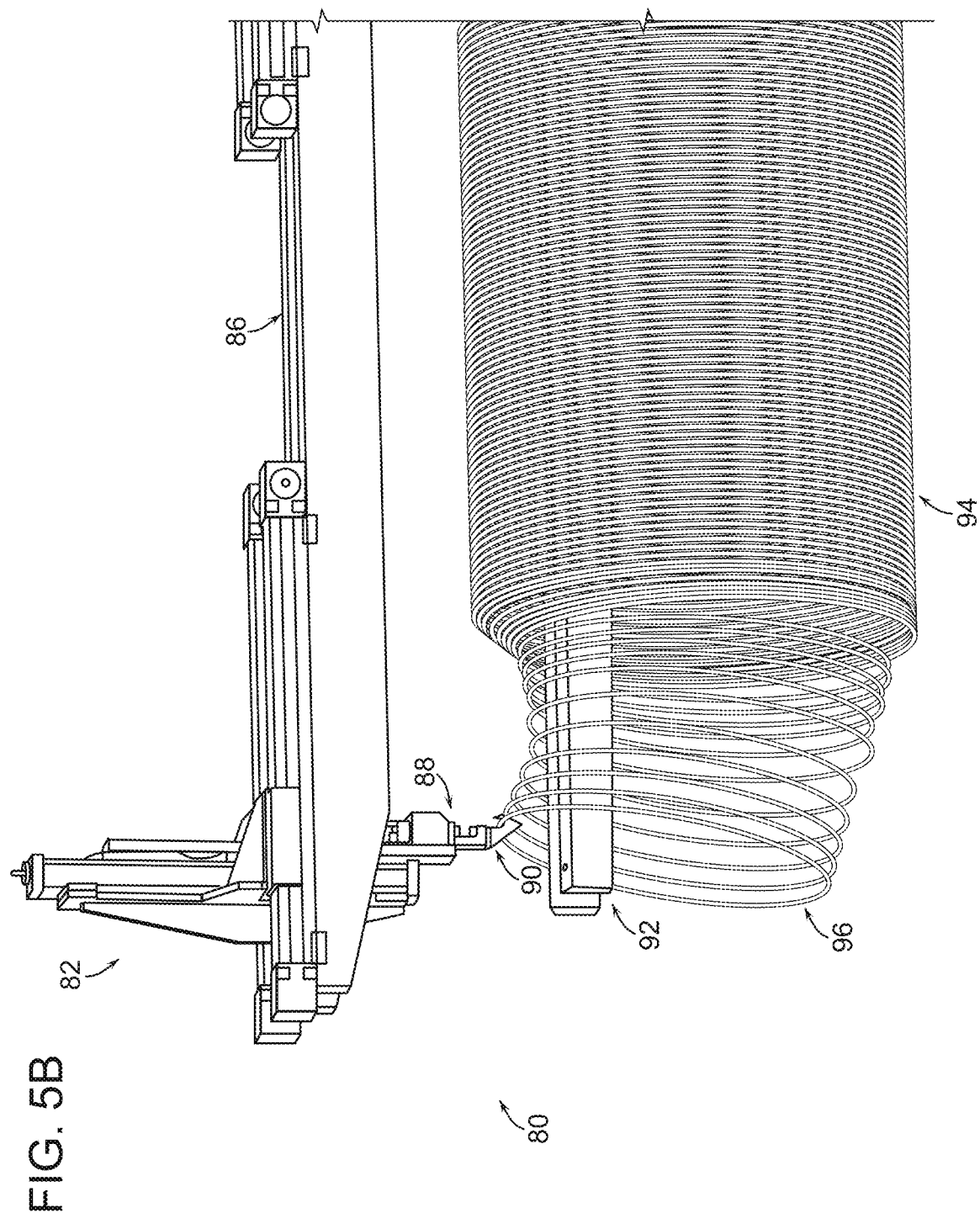

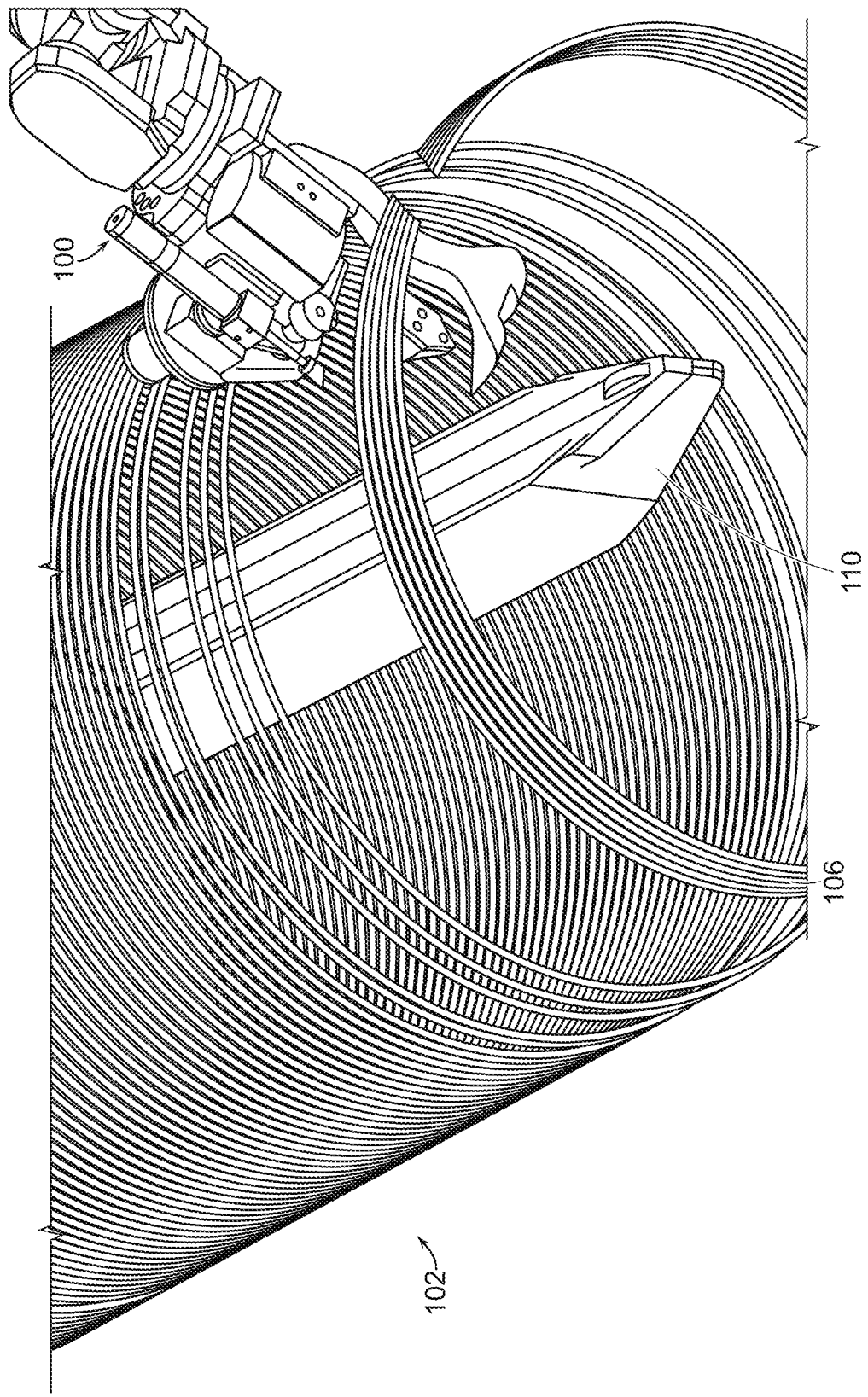

AUTOMATED WIRE ROD TRIMMING STATION AND SAMPLE QUALITY EVALUATION

PRIORITY INFORMATION

This application is a continuation-in-part of U.S. patent application Ser. No. 16/123,347 filed Sep. 6, 2018, which claims priority from U.S. Provisional Application Ser. No. 62/645,446 filed Mar. 20, 2018, all of which are incorporated herein by reference.

BACKGROUND OF THE INVENTION

The invention relates to the field of wire rod-trimming station, and in particular to an automated wire rod-trimming station.

Traditionally an inline high speed shear would be utilized to trim the head and tail of each billet "coil" rolled in the mill, the high speed shear is positioned directly before the laying head in the wire rod line and as a result must be able to trim 5.5 mm wire while travelling at 120-130 m/s. This results in a complex, machine with a complicated control system requiring high maintenance, and attention to detail to operate it correctly and consistently. Due to the complex nature of this machine it has a high capital cost and has a high operating cost as the machine utilizes two main guides, two motors of 200-300 kW and multiple switch pipes that need changing per material size to be trimmed.

SUMMARY OF THE INVENTION

According to one aspect of the invention, there is provided an automated trimming system. The automated trimming system includes a coil that includes a plurality of rings. One or more trimming mechanisms select a number of rings from the coil and proceed to form a sample by cutting a portion of the rings. A receiver unit receives the sample from the one or more trimming mechanisms to evaluate the quality of the sample.

According to another aspect of the invention, there is provided a method of performing the operations of an automated trimming system. The method includes providing a coil that includes a plurality of rings. Also, the method includes selecting a number of rings from the coil and proceed to form a sample by cutting a portion of the rings using one or more trimming mechanisms. Furthermore, the method includes receiving the sample from the one or more trimming mechanisms, using a receiver unit, to evaluate the quality of the sample.

According to another aspect of the invention, there is provided an automated trimming system. The automated trimming system includes a vision system that identifies the number of rings positioned within a coil and sheared positions where the rings need to be cut. One or more trimming mechanisms receive the sheared positions and proceed to cut the rings at the sheared positions. A hook arrangement interfaces with the coil for transferring the coil to a trimming area, once the coil is positioned in the trimming area the ends of the coil are separated to expose the rings positioned within using a plurality of screw rolls or the one or more trimming mechanisms.

According to another aspect of the invention, there is provided a method of performing the operations of an automated trimming system. The method includes identifying the number of the rings positioned within a coil and sheared positions where the rings need to be cut using a vision system. Also, the method includes using one or more trimming mechanisms that receive the sheared positions and proceed to the cut the rings at the sheared positions. A hook arrangement is provided that interfaces with a coil handling area for transferring the coil to a trimming area. Furthermore, the method includes separating the ends of the coil handling system to expose the plurality rings positioned within using a plurality of screw rolls or the one or more trimming mechanisms.

BRIEF DESCRIPTION OF THE DRAWINGS

FIGS. 5A-5C are schematic diagrams illustrating another embodiment of the trimming station used in conjunction with a coil handling system; and FIGS. 6A-6B shows another embodiment of the invention where a sample of a coil is used to test its quality.

DETAILED DESCRIPTION OF THE INVENTION

The invention involves an autonomous trimming station to be included in the coil handling area, in this area the coil has already been formed and collected and is either transported on a pallet or hook conveyance to the compactor for tying. Prior to the compactor, a new station will be included to allow the head and the tail of each coil to be trimmed automatically without operator intervention. The trim station will included a side transfer with a unique hook arrangement to allow the ends of the coils to be spread out to enable trimming of the desired number of head and tail end rings, the cutting or trimming of the rings will be made by an autonomous trimming robot, controlled via a vision system interface. The purpose of the vision system is to ensure the correct number of rings is trimmed from each coil.

Performance of a high speed shear depends on mill speed, whereas the current invention is not subjected to such limitations. For example, when mill speed is 120 m/s, the cutting time for a high speed shear is less than 0.05 seconds, whereas the cutting time for the current invention is approximately 45 seconds. With the concept of trimming in the coil handling area the coil can be trimmed while stationary, a single coil may be held stationary from a minimum time of approximately 45 secs and up depending on the production rate of the mill. The invention works within the coil handling system, via a coil down ender which is a standard product if the initial part of the coil handling system is a vertical pallet system.

A custom designed hook arrangement then interfaces with the down ended coil to remove the coil and transfer the coil to the trimming station. The hook incorporates two ring separating devices that fans out the head and tail ends of the coil by a predetermined amount. This fanning may also be carried out by the trimming robot. This fanning of the coil then allows the vision system to then calculate the number of rings separated from the coil and instruct the arms of trimming robots to position the ring/rings to be cut at the shear locations. The rings are cut using a hydraulic, shear and the arms of the trimming robots then remove the discard rings from the hook before the hook places the coil back on the down ender that then up ends the coil so that it may be transferred to the compactor for processing. If the coil is on a hook arrangement the process is similar but the down ending of the coil is not needed and the coil is transferred from hook to hook.

Figure 1A:
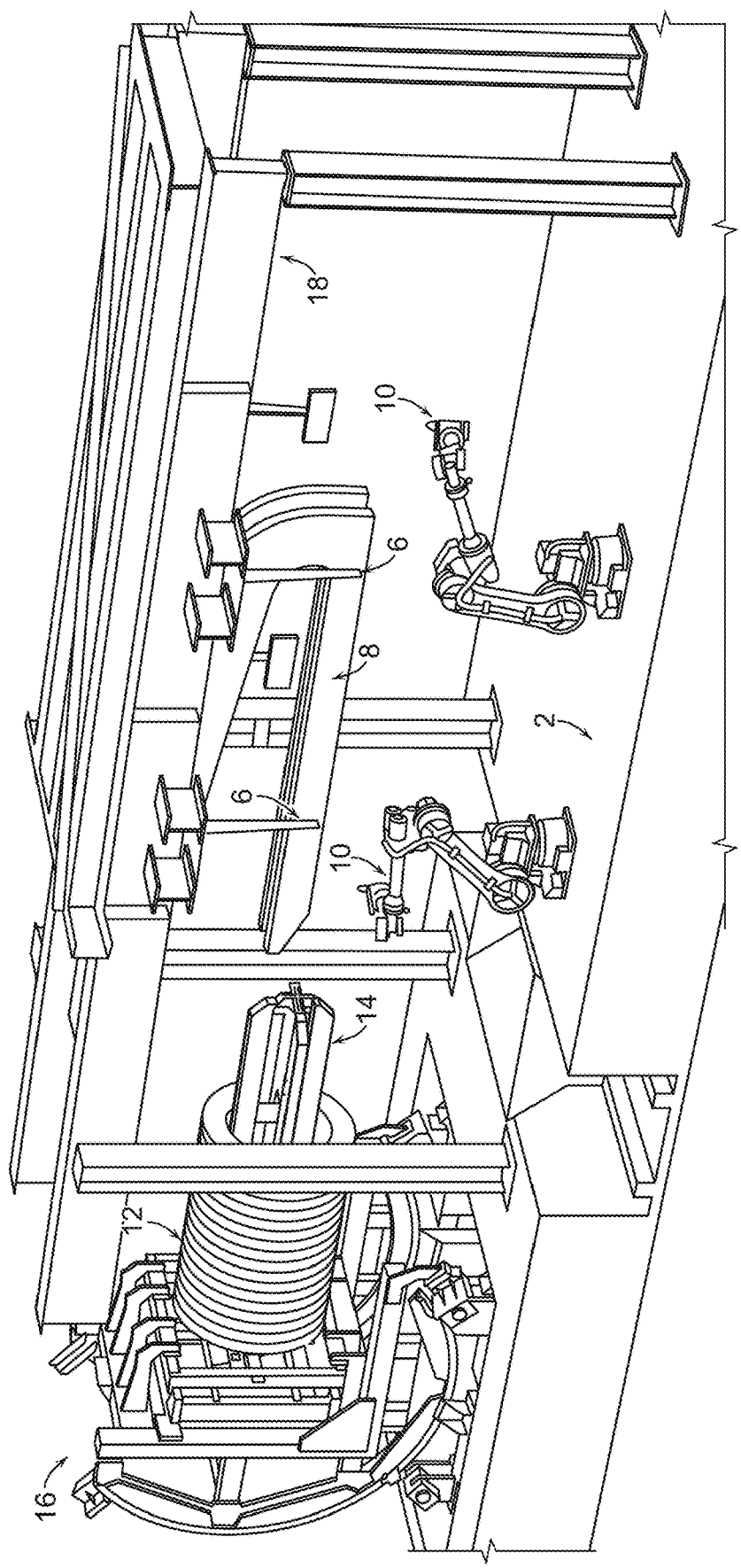
FIGS. 1A-1C are schematic diagrams illustrating a novel trimming station used in conjunction with a coil handling system.
Figure 1B:
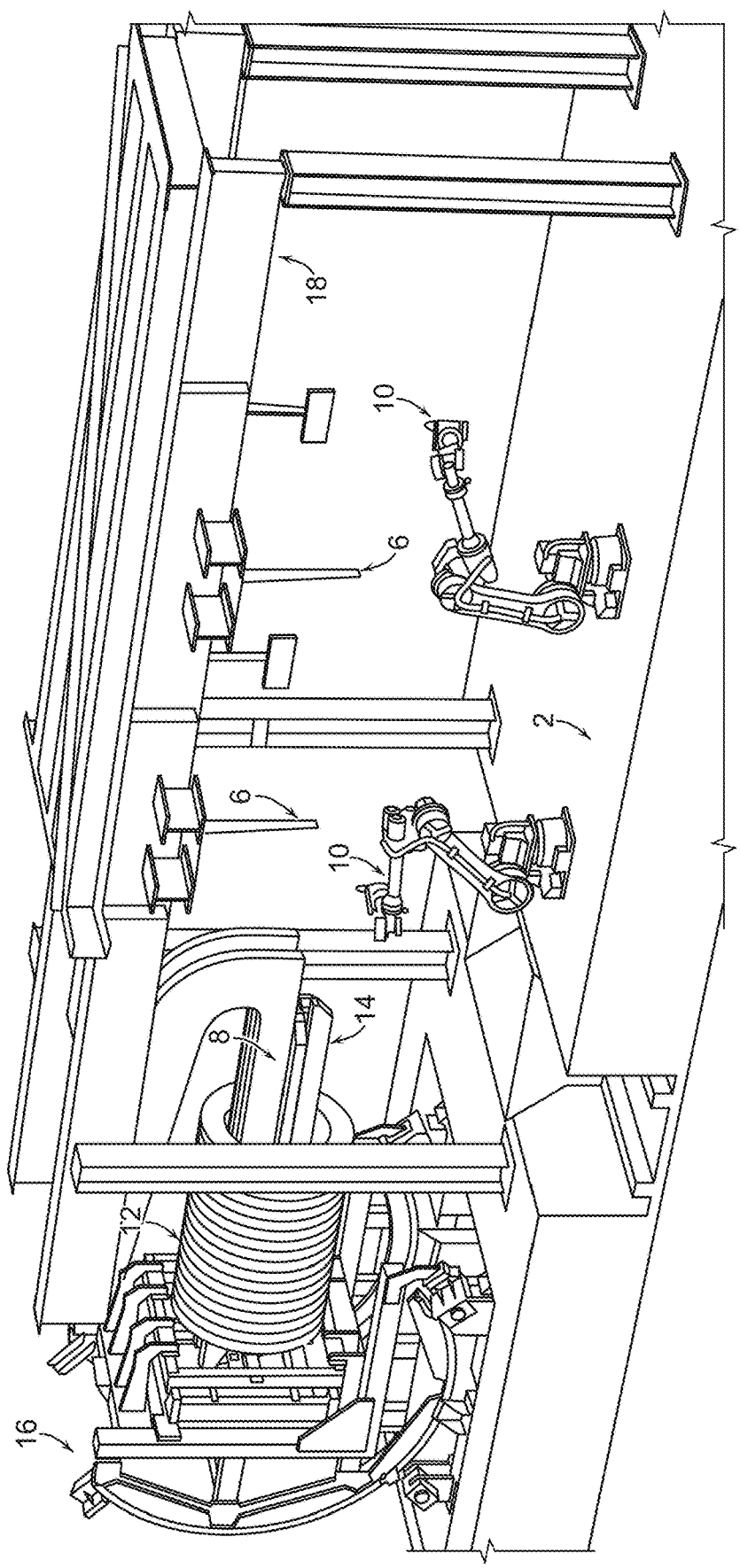
Figure 1C:
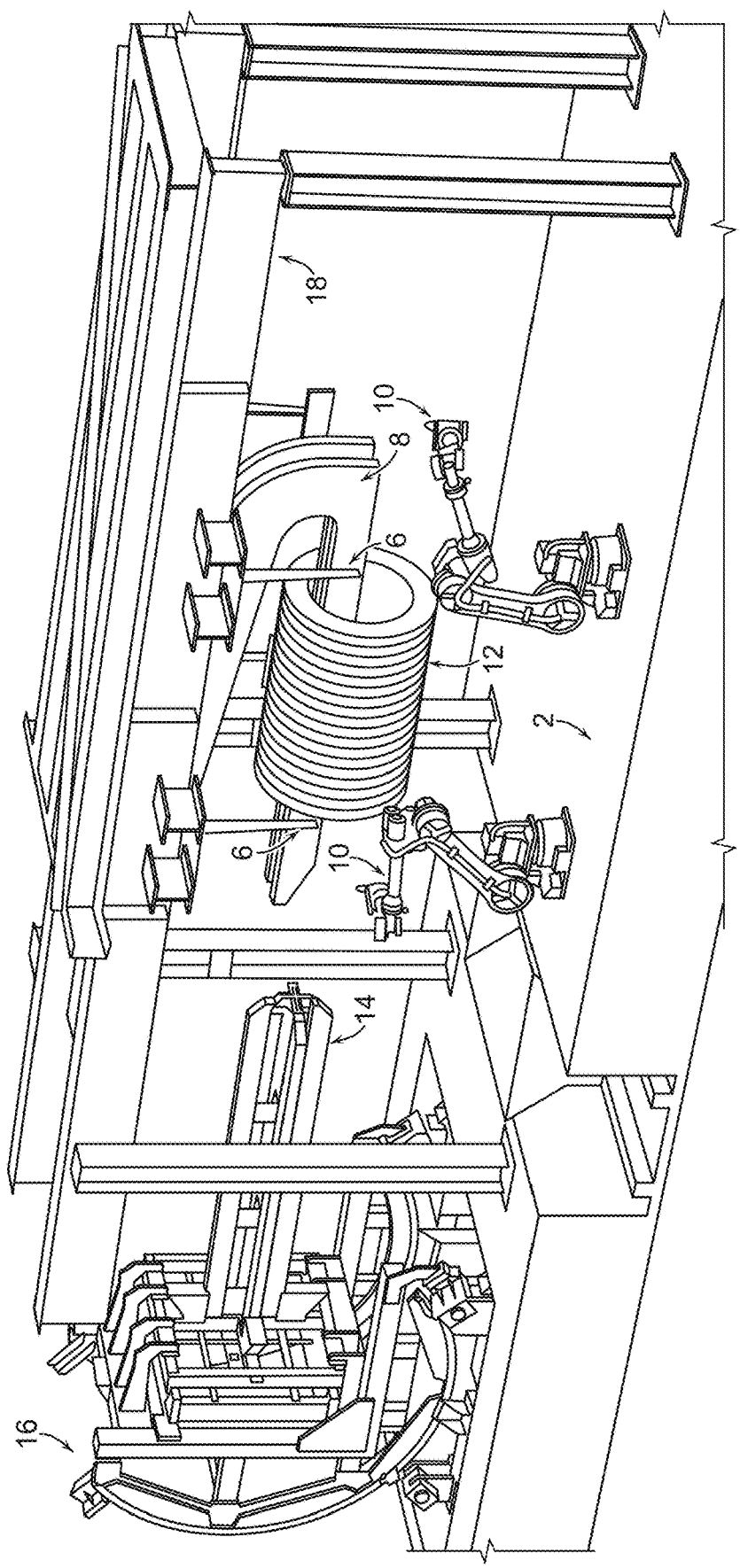

FIGS. 1A-1C are schematic diagrams illustrating the novel trimming station 2 used in accordance with the invention. A coil 12 is positioned on a mandrel 14 that is part of an on-center pallet downender 16. The trimming station 2 includes a hook arrangement 8 and a number of trimming robots 10. As shown in FIG. 1A, the coil 12 is brought to the downender 16 after being processed. The area surrounding mandrel 14 includes a number of lasers to measure and ensure accurate centering of the coils. A hook arrangement 8 is provided that interfaces with the mandrel 14 so as to transfer the coils, as shown in FIG. 1B, to the trimming station 2, as shown in FIG. 1C. The hook arrangement 8 allows the ends of the coil to be spread out to enable trimming of the desired number of head and tail end rings once at the trimming station 2.

There are a number of cameras 6 used as part of a vision system to detect the shape and edges of the coils. At the trimming station 2, the cameras are mounted on rails 18 allowing for easy movement across the coil 12. The trimming robots 10 help spread the ends of the coil 12 to expose the rings laid within. The vision system analyzes these rings using the cameras 6 to correctly identify the number of rings and their respective positions. Using information detected by the vision system, the trimming robots 10 correctly identify the number of rings to be trimmed from each coil. The trimming robots have selective shears specifically designed for trimming.

Figure 2:
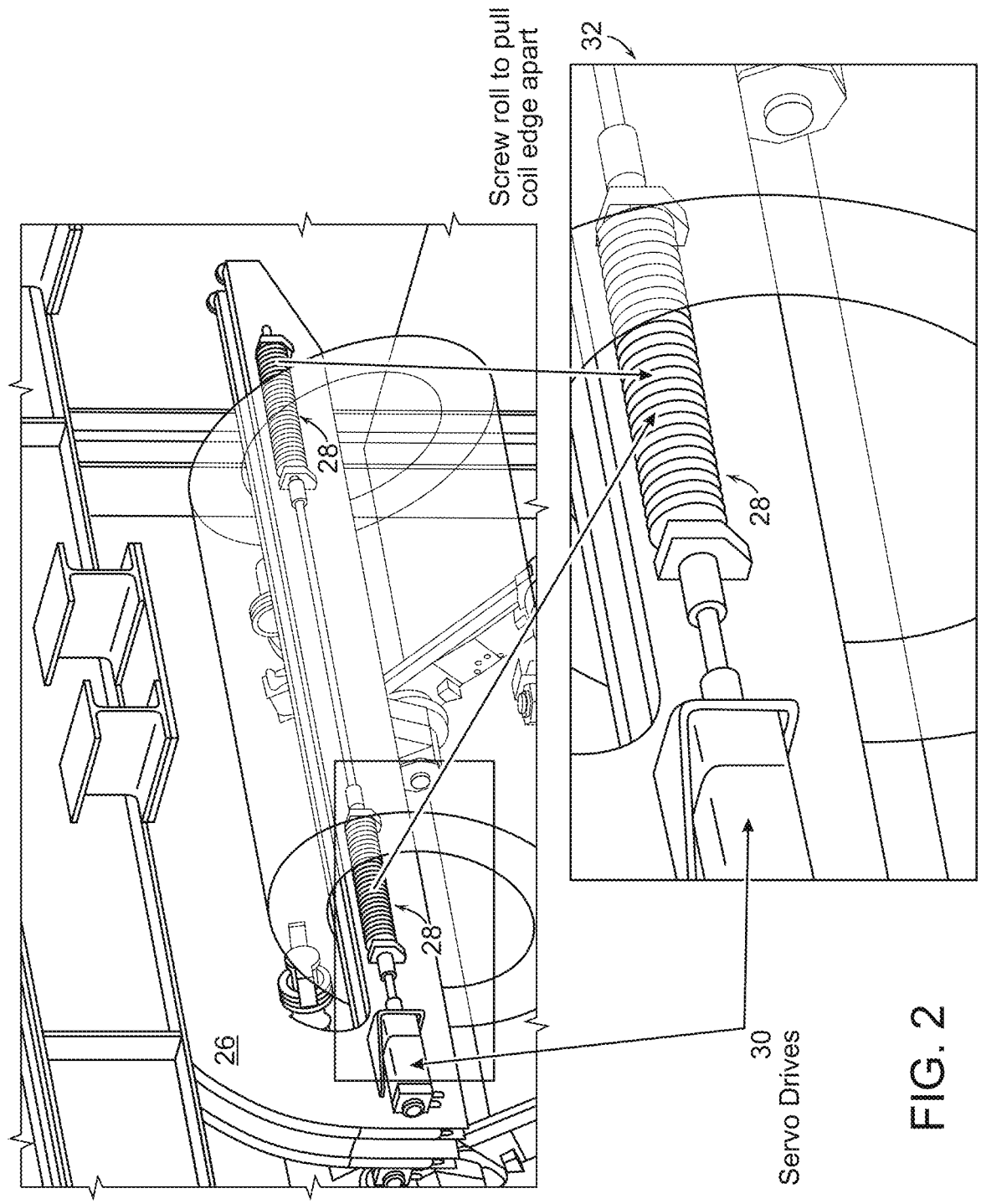
FIG. 2 is a schematic diagram illustrating a detailed view of a novel hook arrangement used in accordance with the invention.

FIG. 2 is a schematic diagram illustrating a detailed view of the hook arrangement 26. The hook arrangement 26 includes a number of screw rolls 28 that are attached on each of its sides. Once the hook arrangement 26 transfers the coil to the trimming station, the screw rolls 28 are used to pull the ends of the coil a certain distance to produce ring separation via one of the trimming robots. A number of servo drives 30 on each side of the hook arrangement are used to pull automatically the end of the coil. The vision system calculates the number of rings at the ring separation and instructs the robotic arms to position the ring/rings to be cut at the shear locations. The inset 32 shows a detailed view of the screw rolls used in accordance with the invention. The vision system and trimming robots communicate with each other via a wireless or wired control system to coordinate the identification and trimming operation.

Figure 3A:
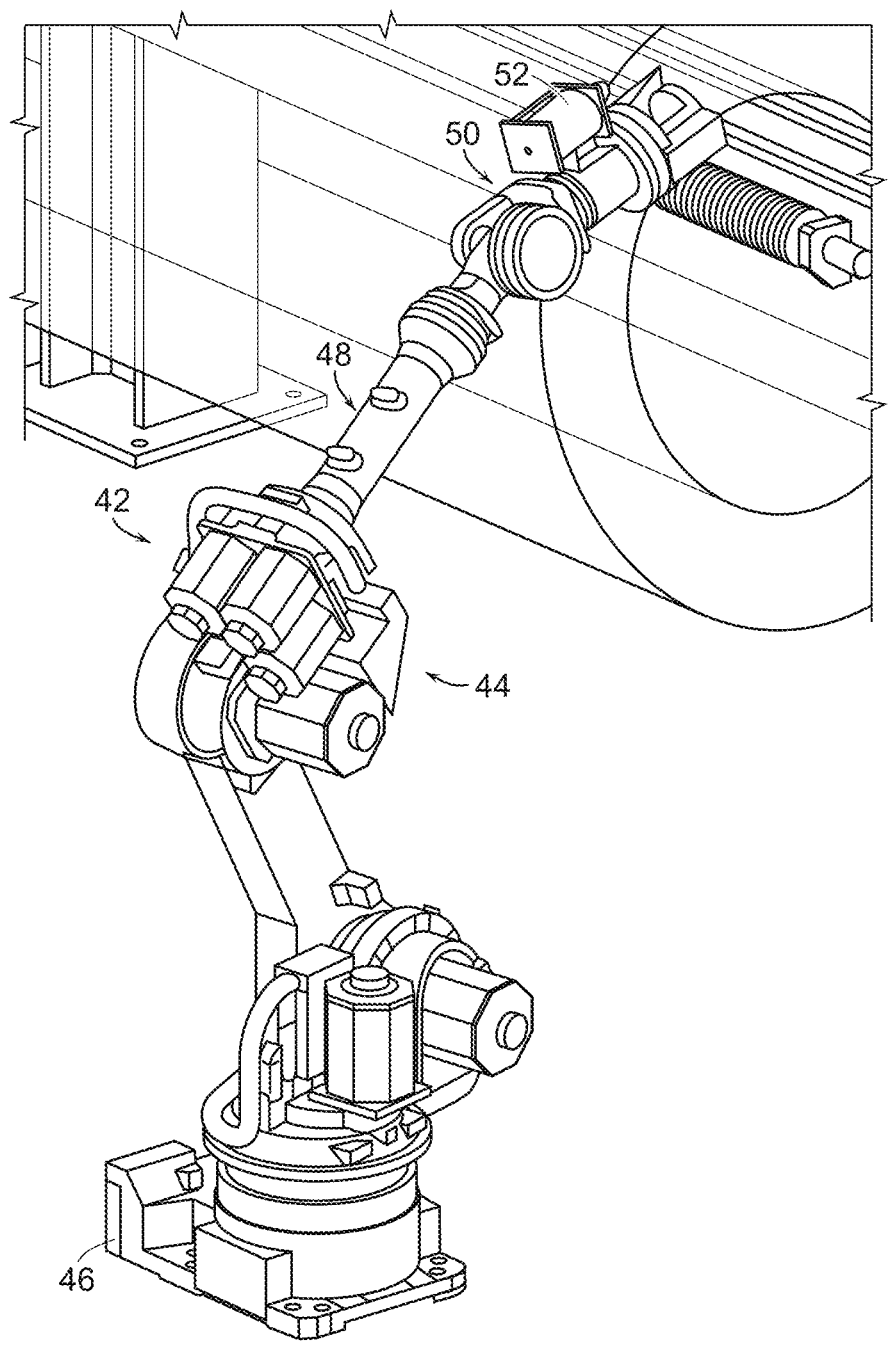
FIGS. 3A-3B are schematic diagrams illustrating a detailed view of a trimming robot.
Figure 3B:
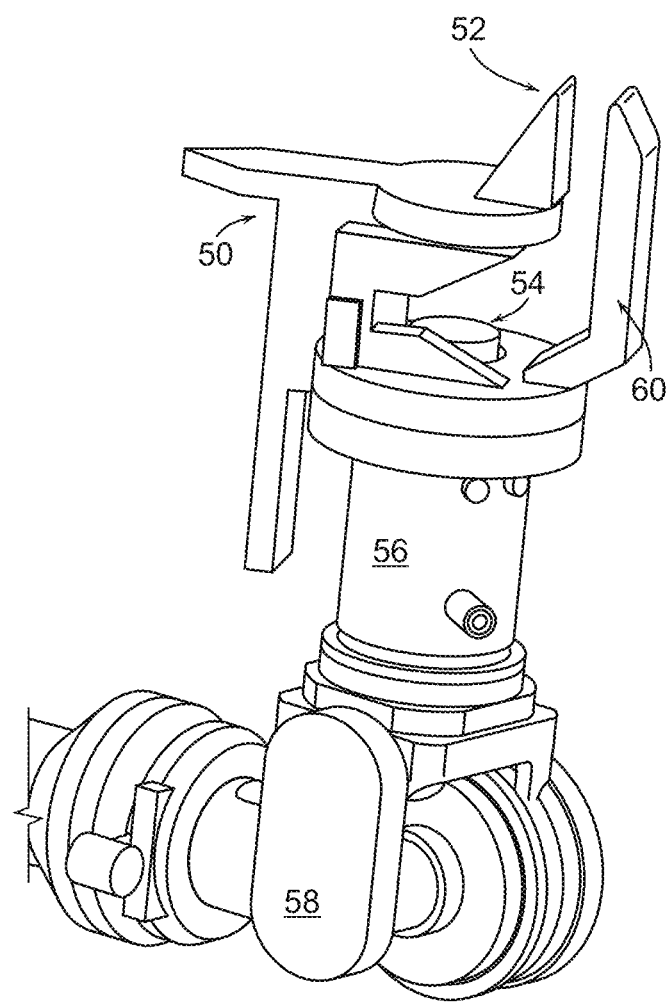

Alternatively the fanning of the coil rings may be carried out by the robot itself, using a custom trimming tool, that is designed in a way to allow multipurpose use, the tool incorporates a fanning tool, the afore mentioned cutting tool and a clamping tool, to carry the cut rings to a discard position FIG. 3A is a schematic diagram illustrating a detailed view of a trimming robot 42 used in accordance with the invention. The trimming robot 42 includes an arm arrangement 44 that is coupled to a stationary surface via a stabilizer system 46. The arm arrangement 44 is coupled to a rotating shaft 48. The rotating shaft 48 is coupled to a lance and shear mechanism 50. FIG. 3B shows a detailed view of the lance and shear mechanism 50. The lance and shear mechanism 50 includes a lance 52 used to fan or separate the coils and a cutter mechanism 54 is used for trimming a coil. A grip item 60 is also included. The lance 52 and cutter and grip mechanism 54 are both positioned on a rotatable shaft 56 permitting the lance 52, the cutter mechanism 54, and the grip item 60 to rotate when in operation. The rotatable shaft 56 is positioned on an anchor mechanism 58 that permits the lance 52, the cutter mechanism 54, and the grip item 60 to move laterally when in operation.

The trimming robot 42 is a 6 axis unit that allows for flexible motion within 6 degrees of freedom. As discussed earlier, the trimming robot 42 works using information collected by one or more of the cameras 52 of the vision system to determine the appropriate positions to cut rings at various shear locations.

Figure 4B:
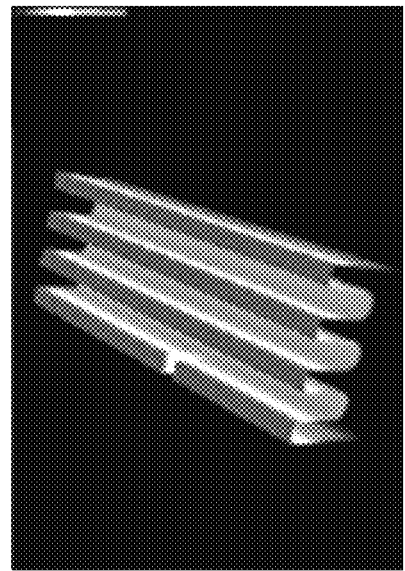
FIGS. 4A-4C are schematic diagrams illustrating the various operations of the vision system.
Figure 4C:
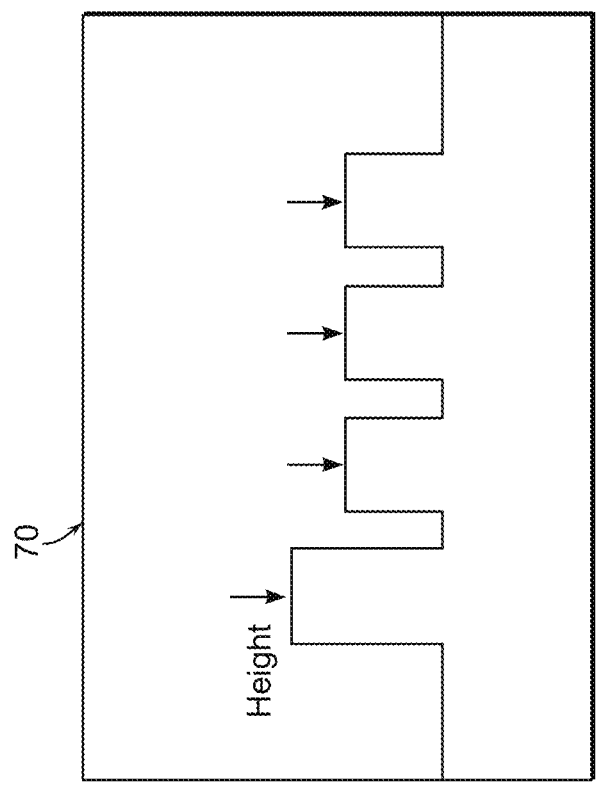
Figure 4A:
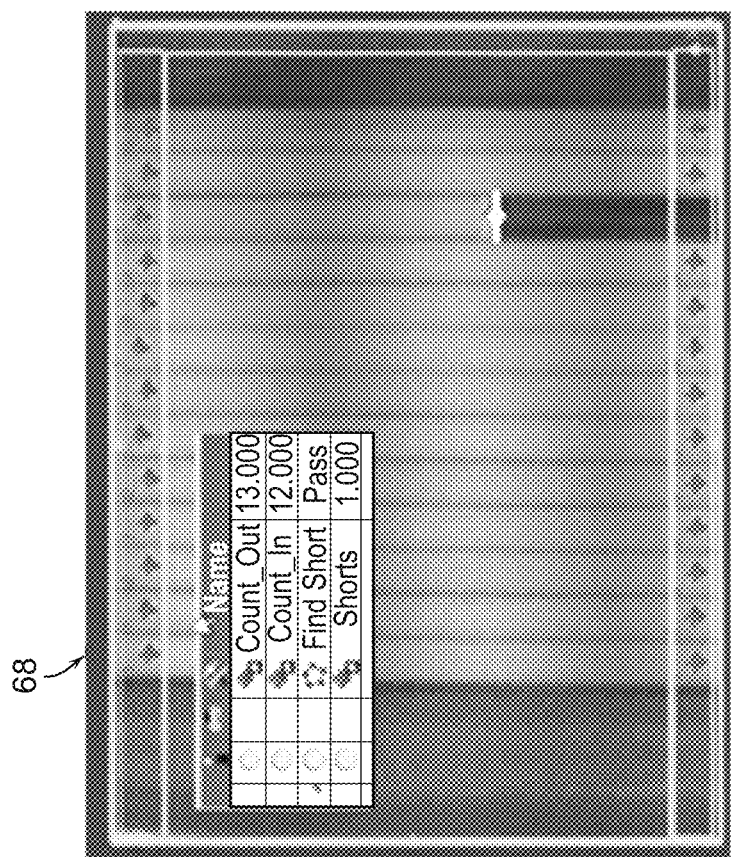

FIGS. 4A-4C are schematic diagrams illustrating the various operations of the vision system. FIG. 4A shows the profile 68 of the various coil ends positioned between the ring separation. The position of each ring is indexed by its location and sent to a controller. The controller uses this information to control the accurate positioning of trimming robots for shearing. FIG. 4B shows the edge/object detection 70 developed by the vision system to detect the appropriate edges of the rings. This information is provided to the controller for processing. FIG. 4C shows the depth of the field 72 of the rings being examined and the vision system provides this information to the controller. After receiving the various information mentioned above by the vision system, the controller evaluates the information and send respective commands to the trimming robots as to which of the evaluated rings are to be sheared and discarded.

Figure 5A:
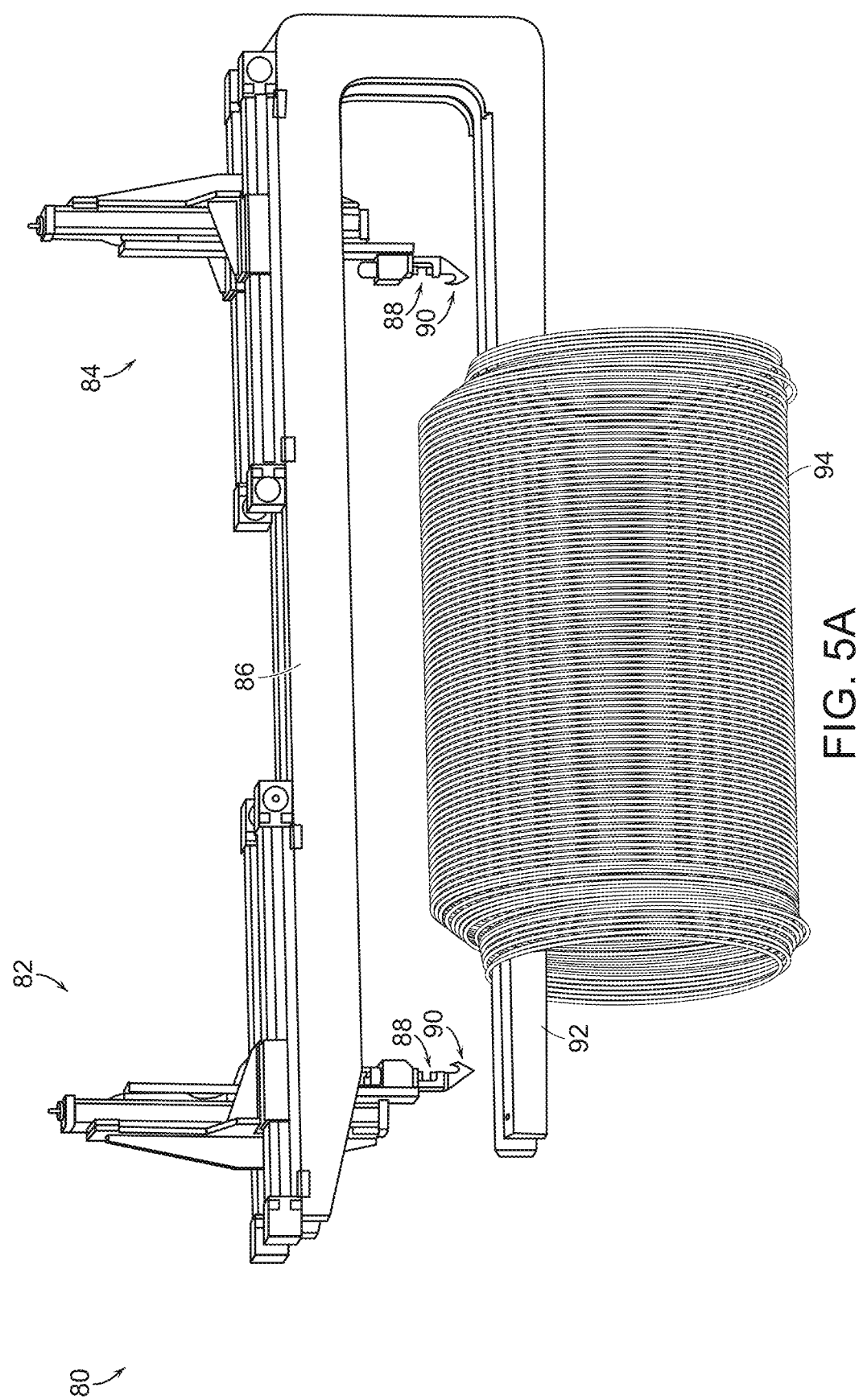
Figure 5C:
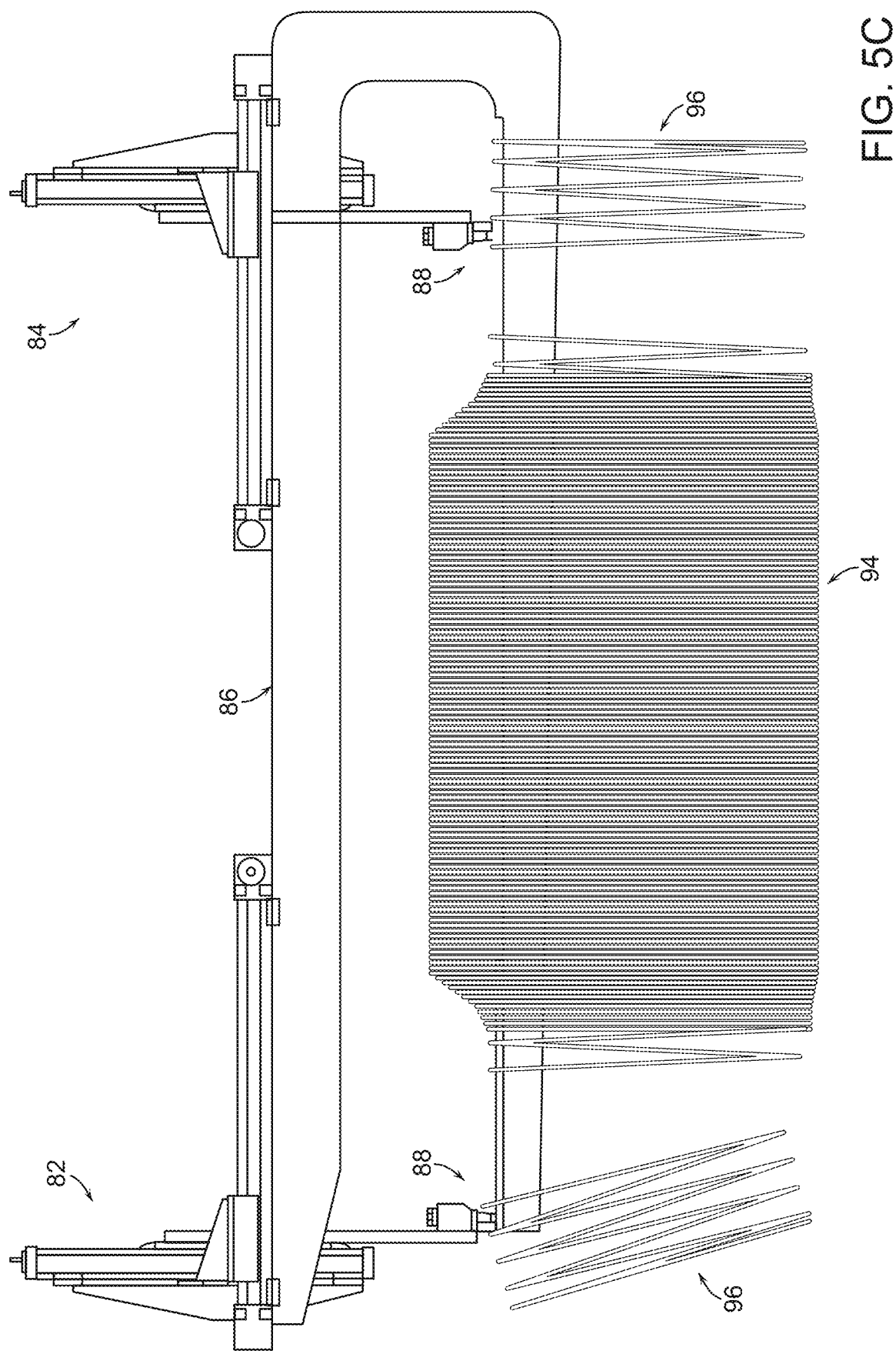

FIGS. 5A-5C are schematic diagrams illustrating another embodiment of the invention. This embodiment 80 uses a pair of trimming systems 82, 84 positioned on a rail 86 that is placed above a hook arrangement 90 and a coil 94 that allows for easy movement, as shown in FIG. 5A. The hook arrangement 90 performs similarly like the aforementioned hook arrangement 8. In particular, the hook system 90 places the coil 94 in a trimming station for further processing. Each trimming system 82, 84 includes a wire cutter 88 and a hook assembly 90. Moreover, the hook assembly 90 of the trimming systems 82 is hooked to the edge of the coil 94 so as to separate the rings 96 over a latch 92 of the hook arrangement 90, as shown in FIG. 5B. The same occurs for the other trimming system 84 where the trimming systems 82, 84 are both separating the rings 96 on both ends of the coil 94 simultaneously or separately over the latch 92.

After placing the rings 96 on the latch 92, the trimming systems 82, 84 trim or cut respective ring 96 at selective locations using their wire cutters 88 at both ends of the coil 94, as shown in FIG. 5C. The determination of these specified locations is provided to the trimming systems 82, 84 by the vision system described herein. A controller is used to interface between the trimming systems 82, 84 and vision system for cutting or trimming the rings 96.

Figure 6B:
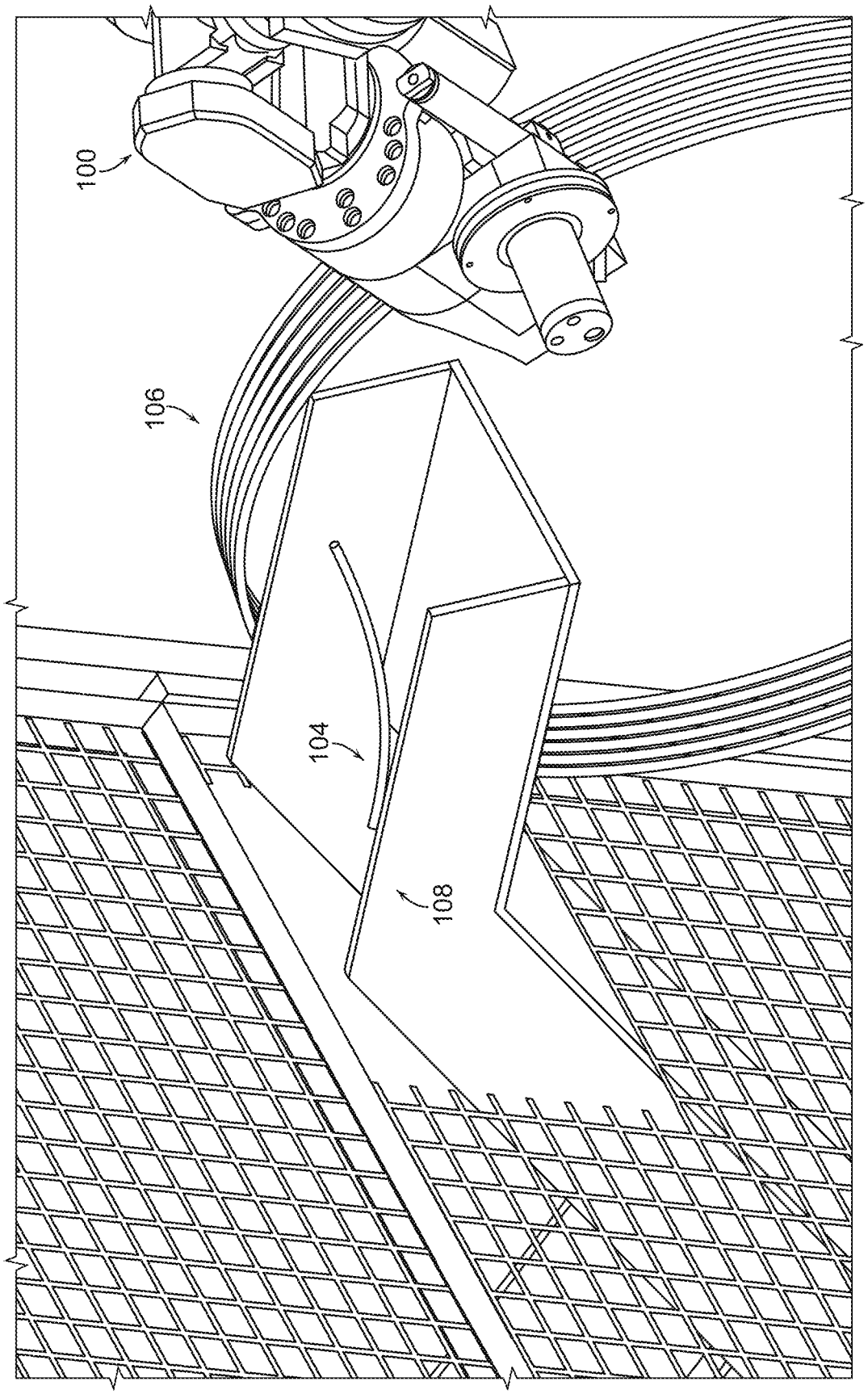

FIGS. 6A-6B shows another embodiment of the invention where a sample of a coil is gathered for a quality test. FIG. 6A shows a trimming robot 100 selecting a predefined number of rings 106 from a coil 102 that is positioned on a hook 110. A gripper rollers assembly, that is a part of end effector, allow variation in length of sample to be cut. FIG. 6B shows the trimming robot 100 trimming a sample 104 from the coils and a receiver unit 108 receives the sample 104. A controller coupled to the trimming robot 100 provides the trim locations for trimming the sections of the rings 106 forming the sample 104. Also, the sample 104 is later analyzed for its metallurgical or mechanical properties to determine if it meets a certain quality. The testing of the sample 104 can occur at the other end of the receiver unit 108 or user can manually pick up the sample from the receiver unit and perform the necessary testing, or can make use of an automated system for picking up and testing the sample. The receiver unit 108 can include an inclined structure such as channel or a slide structure, or the like. Also, the invention does allow for more than one trimming robot 100 to select samples at different points of a coiled system for testing.

Although the present invention has been shown and described with respect to several preferred embodiments thereof, various changes, omissions and additions to the form and detail thereof, may be made therein, without departing from the spirit and scope of the invention.

What is claimed is:

1. An automated trimming system comprising:
   a vision system configured to identify a plurality of rings in a coil that is positioned within a trimming area in the automated trimming system and configured to identify one or more sheared positions where the plurality of rings needs to be cut;
   one or more trimming mechanisms configured to receive the identified one or more sheared positions from the vision system and configured to cut the plurality of rings at the identified one or more sheared positions; and
   a fully automated hook arrangement configured to interface with the coil to transfer the coil to the trimming area, and when the coil is positioned in the trimming area, the hook arrangement configured to separate ends of the coil to expose the plurality of rings positioned within using a plurality of screw rolls or the one or more trimming mechanisms, wherein
   said one or more trimming mechanisms comprises one or more trimming robots, said vision system and trimming robots communicate with each other to coordinate identification and trimming operations.

2. The automated trimming system of claim 1, wherein the hook arrangement interfaces with a coil handling area to transfer the coil to the trimming area.

3. The automated trimming system of claim 1, wherein screw rolls are each positioned on a proximal side and a distal side of the hook arrangement.

4. The automated trimming system of claim 1, wherein the vision system comprises a plurality of cameras.

5. The automated trimming system of claim 4, wherein the cameras are positioned on a rail to allow examination of the rings positioned within the separated ends of the coil.

6. The automated trimming system of claim 1, wherein the vision system produces a profile of the exposed rings.

7. The automated trimming system of claim 1, wherein the vision system detects one or more edges of the exposed coils.

8. The automated trimming system of claim 1, wherein the vision system produces a depth of field view of the exposed coils.

9. The automated trimming system of claim 1, wherein the one or more trimming robots receive commands for shearing the exposed rings via a controller.

10. The automated trimming system of claim 1, wherein the one or more trimming robots fan the rings to be trimmed.

11. The automated trimming system of claim 1, wherein the one or more trimming mechanisms comprise a wire cutter and a hook assembly.

12. The automated trimming system of claim 11, wherein the hook assembly is used to separate the coil to expose the rings.

13. A method of performing the operations of an automated trimming system comprising:
   identifying a plurality of the rings in a coil that is positioned within a trimming area in the automated trimming system;
   identifying, using a vision system, one or more sheared positions where the plurality of rings needs to be cut;
   receiving, at one or more trimming mechanisms, the one or more sheared positions identified by the vision system, the one or more trimming mechanisms cutting the plurality of rings at the identified sheared positions, said one or more trimming mechanisms comprises one or more trimming robots;
   providing a fully automated hook arrangement that interfaces with a coil handling area for transferring the coil to a trimming area; and
   when the coil is positioned in the trimming area, the hook arrangement separating ends of the coil to expose the plurality of rings positioned within using a plurality of screw rolls or the one or more trimming mechanisms, wherein
   said vision system and trimming robots communicate with each other to coordinate identification and trimming operations.

14. The method of claim 13, wherein the hook arrangement interfaces with a coil handling area to transfer the coil to the trimming area.

15. The method of claim 13, wherein the screw rolls are each positioned on a proximal side and a distal side of the hook arrangement.

16. The method of claim 13, wherein the vision system comprises a plurality of cameras.

17. The method of claim 16, wherein the cameras are positioned on a rail to allow examination of the rings positioned within the separated ends of the coil.

18. The method of claim 13, wherein the vision system produces a profile of the exposed rings.

19. The method of claim 13, wherein the vision system detects one or more edges of the exposed coils.

20. The method of claim 13, wherein the vision system produces a depth of field view of the exposed coils.

21. The method of claim 13, wherein the one or more trimming robots receive commands for shearing the exposed rings via a controller.

22. The method of claim 13, wherein the one or more trimming robots fan the rings to be trimmed.

23. The method of claim 13, wherein the one or more trimming mechanisms comprise a wire cutter and a hook assembly.

24. The method of claim 23, wherein the hook assembly is used to separate the coil to expose the rings.

* * * * *